(12) United States Patent
Himmler

(10) Patent No.: US 7,629,476 B2
(45) Date of Patent: Dec. 8, 2009

(54) METHOD FOR PRODUCING 2,5-DIMETHYLPHENYL ACETIC ACID

(75) Inventor: Thomas Himmler, Odenthal (DE)

(73) Assignee: Bayer Cropscience AG, Monheim (DE)

( * ) Notice: Subject to any disclaimer, the term of this patent is extended or adjusted under 35 U.S.C. 154(b) by 0 days.

(21) Appl. No.: 12/388,274

(22) Filed: Feb. 18, 2009

(65) Prior Publication Data

US 2009/0156839 A1 Jun. 18, 2009

Related U.S. Application Data

(62) Division of application No. 10/586,491, filed as application No. PCT/EP2005/000617 on Jan. 22, 2005, now Pat. No. 7,579,500.

(30) Foreign Application Priority Data

Feb. 4, 2004 (DE) ........................ 10 2004 005 318

(51) Int. Cl.
C07D 319/06 (2006.01)
(52) U.S. Cl. ..................................... 549/369
(58) Field of Classification Search .................. 549/369
See application file for complete search history.

(56) References Cited

FOREIGN PATENT DOCUMENTS

| DE | 33 22 459 A1 | 1/1984 |
|---|---|---|
| EP | 0 034 871 A2 | 9/1981 |
| EP | 0 101 124 A1 | 2/1984 |
| WO | WO 97/36868 A1 | 10/1997 |

OTHER PUBLICATIONS

Friedman, L. and Koca, R., "Anomalies in the Acetylation of o- and p-Xylenes," J. Org. Chem. 33:1255-1257, American Chemical Society (1968).
Giordano, C., et al., "Synthesis of Anti-Inflammatory α-Arylalkanoic Acids by 1,2-Aryl Shift," Agnew Chem. Int. Ed. Engl. 23:413-419, Verlag Chemie (1984).
Hart, H., et al.,"1,4,5,8,9-Pentamethylanthracene. Synthesis and Protonation," Tetrahedron Lett. 52:4639-4642, Pergamon Press (1975).
Khurana, J.M. and Maikap, G.C., "Bromomethylation of aromatics mediated by low frequency ultrasound," J. Indian Chem. Soc. 76:216-217, The Indian Chemical Society (1999).
Kumar, A., et al., "Facile 1,2-Aryl Migration of 2-Halomethyl-2-(4'-Hydroxy-Phenyl) Ketals: A Novel Single Step Synthesis of 4-Hydroxyphenylacetic Acid & Its Derivatives," Syn Commun 27:1133-1141, Marcel Dekker, Inc. (1997).
Kunckell, F., "Ueber einige halogenisirte Ketone," Chem. Ber. 30:577-579, Verlag Chemie (1897).
English language translation for Kunckell, F., "Some Halogenated ketones," Chem. Ber. 30:577-579, Verlag Chemie (1897).
Newman, M.S. and Layton, R.M., "Free-Radical 1:5 Rearrangement of the Trichloromethyl Group," J. Org. Chem. 33:2338-2342, American Chemical Society (1968).
Smith, L.I. and MacMullen, C.W., "The Reaction between Quinones and Sodium Enolates. IV. Pseudocumoquinone, Sodium Acetoacetic Ester and Sodium Malonic Ester," J. Amer. Chem. Soc. 58:629-635, American Chemical Society (1936).
Vallejos, J.C., et al., "A new system for the reduction of 4-hydroxymandelic acids," Bull. Soc. Chim. Fr. 134:101-104, Elsevier (1997).
Vejdělek, Z.J., et al., "6-Aminopenicillansäure-Derivate II. Substituierte 6-N-(2-Styryl- Und 6-N-(2-Phenyläthyl-Benzamido)Penicillansäuren," Collect. Czech. Chem. Commun. 29:776, 786-788, 791-794, Nakladatelstvi Ceskoslovenski Akademie Ved (1964).
STNEasy Database, Accession No. 1964:82833, English language abstract for Vejdělek, Z.J., et al., "Derivatives of 6-Aminopenicillanic acid. II. Substituted 2'-styryl and 2'-phenethyl derivatices of 6-benzamidopenicillanic acid," Collect. Czech. Chem. Commun.29: 776, 786-788, 791-794, Nakladatelstvi Ceskoslovenski Akademie Ved (1964).
Zaugg, H.E., et al., "Naphthoquinone Antimalarials. XIV. 2-Hydroxy-3-aryl-1,4-naphthoquinones," J. Amer. Chem. Soc. 70:3224-3228, American Chemical Society (1948).
International Search Report for International Application No. PCT/EP2005/000617, European Patent Office, Netherlands, mailed on Jul. 5, 2005.

Primary Examiner—Taofiq A Solola
(74) Attorney, Agent, or Firm—Sterne, Kessler, Goldstein & Fox P.L.L.C.

(57) ABSTRACT

The invention relates to a method for preparing 2,5-dimethylphenylacetic acid by converting p-xylene with chloroacetyl chloride into 2-chloro-1-(2,5-dimethylphenyl)ethanone, which is reacted with the compound of the formula (II) to give the compound of the formula (III), which is then rearranged to give a mixture of the compounds (IV) and (V), which is then hydrolyzed to 2,5-dimethylphenylacetic acid.

1 Claim, No Drawings

METHOD FOR PRODUCING 2,5-DIMETHYLPHENYL ACETIC ACID

This application is a divisional of application Ser. No. 10/586,491, filed Jul. 20, 2006, now pending, which is a National Stage of International Application No. PCT/EP2005/000617, filed Jan. 22, 2005, which claims the benefit of German Patent Application No. 10-2004-005-318.9, filed Feb. 4, 2004. The entirety of each of these applications is incorporated by reference herein.

The present invention relates to a novel method for preparing 2,5-dimethylphenylacetic acid.

2,5-Dimethylphenylacetic acid is a known compound (for example from: Z. J. Vejdelek et al., Collect. Czech. Chem. Commun. 29 (1964) 776-94). Preparation is possible for example starting from 2,5-dimethylphenylacetophenone by a Willgerodt-Kindler reaction (H. E. Zaugg et al., J. Amer. Chem. Soc. 70 (1948) 3224-8). However, this method results in large quantities of sulfur-containing waste. In addition, volatile sulfur compounds with very offensive odors may occur.

A further method for preparing 2,5-dimethylphenylacetic acid starts from 2,5-dimethylbenzyl bromide. The corresponding nitrile is prepared therefrom, e.g. with sodium cyanide, and is subsequently hydrolyzed. The required 2,5-dimethylbenzyl bromide can be prepared for example by bromomethylation of p-xylene using formaldehyde and hydrogen bromide (H. Hart et al., Tetrahedron Letters 1975, 4639-42; J. M. Khurana and G. C. Maikap, J. Ind. Chem. Soc. 76 (1999) 216-7). However, the disadvantage in this case is that unwanted side reactions may occur to give multiply bromomethylated products. In addition, the occurrence of bisbromomethyl ether cannot be precluded, so that technically elaborate safety measures must be applied here.

A further disclosed possibility for preparing 2,5-dimethylphenylacetic acid consists of starting from 2,5-dimethylbenzyl chloride, preparing the nitrile therefrom (J. Amer. Chem. Soc. 58 (1936) 629-35; J. Org. Chem. 33 (1968) 2338-42) and then hydrolyzing the latter. 2,5-Dimethylbenzyl chloride is likewise known and can be prepared by chloromethylation of p-xylene (Z. J. Vejdelek et al., Collect. Czech. Chem. Commun. 29 (1964) 776-94). However, chloromethylation is a method which can be carried out only with great technical elaboration and high costs, because of the possibility of the highly toxic bischloromethyl ether occurring. In addition, this method provides 2,5-dimethylphenylacetic acid only in unsatisfactory yields (e.g. 38% of theory over 3 stages according to Z. J. Vejdelek et al., Collect. Czech. Chem. Commun. 29 (1964) 776-94).

All the methods disclosed to date for preparing 2,5-dimethylphenylacetic acid accordingly have in some cases considerable deficiencies and disadvantages which make the preparation of 2,5-dimethylphenylacetic acid difficult. Since phenylacetic acids in general, and among them especially also 2,5-dimethylphenylacetic acid, are important precursors for example for active substances in crop protection (cf. WO 97/36868), there is a need for a technically simple and highly efficient method for preparing 2,5-dimethylphenyl acetic acid.

It has now been found that 2,5-dimethylphenylacetic acid can surprisingly be obtained in high yield and purity by initially converting p-xylene with chloroacetyl chloride in a Friedel-Crafts reaction into 2-chloro-1-(2,5-dimethylphenyl) ethanone of the formula (I), preparing from this ketone with a diol of the general formula (II) the corresponding ketal of the general formula (III), then rearranging the latter to a mixture of the corresponding hydroxyalkyl 2,5-dimethylphenylacetates of the general formula (IV) and bis(2,5-dimethylphenylacetic acid) diesters of the general formula (V), and finally hydrolyzing the latter to give 2,5-dimethylphenylacetic acid.

The method of the invention can be illustrated by the following scheme:

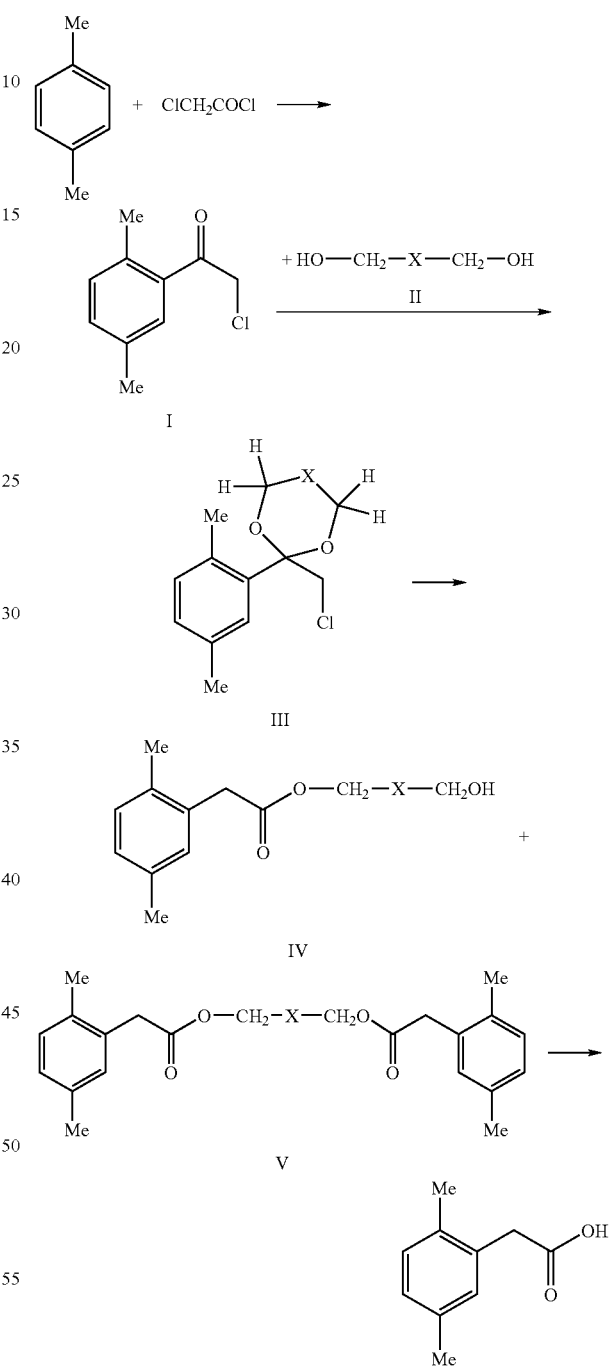

The compound of the formula (I) is known (see, for example, F. Kunckell, Chem. Ber. 30 (1897) 577-579) and can, apart from Friedel-Crafts acylation, also be prepared for example by chlorination of 2,5-dimethylacetophenone.

In the general formulae (II), (III), (IV) and (V),

X is a direct single bond, $CH_2$, $CHCH_3$, $CHC_2H_5$, $C(CH_3)_2$ or $C(C_2H_5)_2$.

The compounds of the formula (II) are known and commercially available.

The present invention likewise relates to the novel compounds of the general formula (III) in which X is a direct single bond, $CH_2$, $CHCH_3$, $CHC_2H_5$, $C(CH_3)_2$ or $C(C_2H_5)_2$.

Preferred compounds of the general formula (III) are those in which

X is a direct single bond, $CH_2$, $C(CH_3)_2$ or $C(C_2H_5)_2$.

Particularly preferred compounds of the general formula (III) are those in which X is a direct single bond, $C(CH_3)_2$ or $C(C_2H_5)_2$.

It is surprisingly possible by the method of the invention to prepare 2,5-dimethylphenylacetic acid in a simpler manner, with better selectivity and in a higher yield than by methods previously disclosed.

Friedel-Crafts catalysts which can be employed for preparing the compound of the formula (I) by the method of the invention are, for example, aluminum chloride, iron(III) chloride, tin-tetrachloride or zeolites.

Aluminum chloride is preferably employed as Friedel-Crafts catalyst.

The amount of Friedel-Crafts catalyst to be employed in the method of the invention is not critical. Thus, for example, from 0.8 to 1.2 mol of catalyst can be employed per mole of chloroacetyl chloride. From 0.9 to 1.1 mol of catalyst per mole of chloroacetyl chloride are preferred.

Solvents employed for the Friedel-Crafts reaction are solvents which are substantially inert in the method of the invention, such as, for example, nitrobenzene, carbon disulfide, methylene chloride, 1,2-dichloroethane or p-xylene itself. Carbon disulfide, 1,2-dichloroethane and p-xylene are preferred. p-Xylene is particularly preferred.

The amount of chloroacetyl chloride to be employed in the method of the invention is not critical and may vary within wide limits. If a solvent is used, for example from 0.8 to 1.2 mol of chloroacetyl chloride per mole of p-xylene can be employed. From 0.9 to 1.1 mol of chloroacetyl chloride per mole of p-xylene are preferred.

If an excess of p-xylene is used as solvent, the ratio of chloroacetyl chloride to p-xylene will of course be distinctly smaller.

Since it is known (see, for example, L. Friedman and R. Koca, J. Org. Chem. 33 (1968) 1255-7), that p-xylene can be isomerized by a Friedel-Crafts catalyst such as $AlCl_3$, the procedure is expediently such that p-xylene and chloroacetyl chloride are mixed, and the Friedel-Crafts catalyst is metered in.

The first step in the method of the invention can be carried out at temperatures between −20 and +60° C. Temperatures between −10 and +30° C. are preferred.

The reaction times for the first step of the method of the invention are between 1 and 24 hours.

In the second step of the method of the invention, the ketal of the general formula (III) is prepared by heating the ketone of the formula (I) with a diol of the general formula (II) in the presence of a catalyst.

Examples which may be mentioned of diols of the general formula (II) are ethylene glycol, 1,2-propanediol (propylene glycol), 1,3-propanediol (trimethylene glycol), 2,2-dimethyl-1,3-propanediol (neopentyl glycol) and 2,2-diethyl-1,3-propanediol. Ethylene glycol and neopentyl glycol are preferred. Neopentyl glycol is particularly preferred.

Catalysts suitable for the second step of the method of the invention are acids such as hydrochloric acid, sulfuric acid, phosphoric acid, methylsulfonic acid, p-toluenesulfonic acid, acidic ion exchangers, inter alia. Hydrochloric acid, sulfuric acid and p-toluenesulfonic acid are preferred.

Solvents suitable for the second step of the method of the invention are inert organic solvents such as, for example, aliphatic and aromatic hydrocarbons, and the diols themselves. Aromatic hydrocarbons are preferably used, particularly preferably xylene itself.

The procedure for preparing the ketal of the general formula (III) in the presence of an acid catalyst is expediently such that the water of reaction is removed by azeotropic distillation with the solvent, preferably the aromatic hydrocarbon.

The rearrangement (1,2-aryl shift) of the ketal of the general formula (III) in the third step of the method of the invention to give the 2,5-dimethylphenylacetic esters of the general formulae (IV) and (V) takes place in a way known in principle by heating in a polar protic solvent in the presence of a weak base (C. Giordano et al., Angew. Chem. 96 (1984) 413-9; EP-A 101 124). A further method for the 1,2-aryl shift of the ketal of the general formula (III) consists of heating in the presence of a Lewis acid such as, for example, $FeCl_2$, $FeCl_3$, $CaCl_2$, $CuCl_2$ or $ZnCl_2$ (EP-A 034 871). It has further been disclosed that the 1,2-aryl shift in substituted 1,3-dioxane ketal derivatives can be carried out with catalytic amounts of a zinc carboxylate salt which is soluble in the reaction mixture, such as, for example, zinc 2-ethylhexanoate (DE-A 33 22 459). The latter methods have the disadvantage, however, that the catalysts such as, for example, zinc compounds must be removed by elaborate methods (precipitation; treatment of the reaction mixture with activated carbon). In addition, chlorinated alcohols are formed as waste products and require disposal.

It has further been disclosed that 2-halomethyl-2-(4'-hydroxyphenyl) ketals can be rearranged to 4-hydroxyphenylacetic acid derivatives by heating with sodium hydroxide solution (A. Kumar and R. A. Rane, Synthetic Commun. 27 (1997) 1133-41). However, this reaction succeeds less well with the chlorine-substituted ketals than with the bromine-substituted ketals. In addition, a special situation is present due to the 4-hydroxy substitution on the aromatic system, because the phenolate ion present in the alkaline medium may, as a result of quinoide contributing structures, greatly influence the reactivity at the ketal group. An influence of this type is also known for example in the case of reduction of 4-hydroxymandelic acids (J. C. Vallejos et al., Bull. Soc. Chim. Fr. 134 (1997) 101-4). It was therefore by no means to be expected from the outset that this method variant would succeed even with other than 4-hydroxyphenyl-substituted chloromethyl ketals.

Polar protic solvents which can be used for the third step of the method of the invention are water, alcohols, diols, polyols and mixtures thereof.

In the mixture of compounds of the formulae (IV) and (V), the X radical may also, within the definition indicated above, have a different meaning than in the formulae (II) and (III), respectively, owing to transesterifications, depending on the solvent used in the third step of the method of the invention. If, for example, the method is carried out in the second step using neopentyl glycol ($X = C(CH_3)_2$ in compound of the formula (II) and (III)), and if then ethylene glycol is used as solvent in the third step of the method of the invention, the mixture of the compounds of the formulae (IV) and (V) may comprise both those with $X = C(CH_3)_2$ and those with X=direct single bond.

The amount of solvent may vary within wide limits. Typically, between 200 ml and 2000 ml of solvent are employed per mole of ketal.

Bases which can be used in the third step of the method of the invention are, for example, alkali metal salts of formic acid, acetic acid, propionic acid or benzoic acid, alkali metal phosphates, carbonates and bicarbonates.

The bases can be employed in amounts of from 1 to 3 mol per mole of ketal. From 1.2 to 1.6 mol per mole of ketal are preferred.

It is also possible in the method of the invention to employ only catalytic amounts of an alkali metal salt of formic acid, acetic acid, propionic acid or benzoic acid, and instead to add sodium hydroxide or potassium hydroxide in addition. Preferably, from 0.1 to 0.3 mol per mole of ketal are used in combination with from 1 to 3 mol of sodium hydroxide or potassium hydroxide per mole of ketal.

From 0.1 to 0.3 mol of sodium acetate per mole of ketal are particularly preferably used in combination with from 1 to 3 mol of sodium hydroxide per mole of ketal.

It is also possible in the method of the invention additionally to dispense completely with the use of an alkali metal salt of formic acid, acetic acid, propionic acid or benzoic acid, and to effect the reaction in the third step solely by adding an alkali metal hydroxide. In this case, the alkali metal hydroxide can be employed in solid form or as aqueous solution.

Potassium hydroxide and sodium hydroxide are preferably used.

In these two embodiments of the third step of the method of the invention, the hydrolysis of the intermediates of the general formulae (IV) and (V) also takes place directly, so that the otherwise usual 4th step of the method can be omitted.

The third step of the method of the invention for preparing 2,5-dimethylphenylacetic acid can be carried out at temperatures between 100 and 250° C. Temperatures between 150 and 230° C. are preferred, particularly preferably between 170 and 220° C.

The reaction times for the third step of the method of the invention are between 1 and 24 hours.

In the fourth step of the method of the invention, the esters of the general formulae (IV) and (V) are hydrolyzed by known methods of organic chemistry to 2,5-dimethylphenylacetic acid.

The hydrolysis preferably takes place by heating with sodium hydroxide solution.

The method of the invention for preparing 2,5-dimethylphenylacetic acid preferably takes the form of carrying out all the steps successively without isolating the intermediates. Time-consuming and costly working up and purification steps such as crystallization, filtration, drying etc. are thus omitted.

It can be said to be particularly surprising that, despite the lack of purification operations on the intermediate stages, the 2,5-dimethylphenylacetic acid is obtained by the method of the invention not only in very high yield but also excellent purity.

Accordingly, the method of the invention for preparing 2,5-dimethylphenylacetic acid is preferably carried out in the following way:

in the first step of the method of the invention, p-xylene undergoes a Friedel-Crafts reaction with chloroacetyl chloride in the presence of aluminum chloride to give 2-chloro-1-(2,5-dimethylphenyl)ethanone. The solvent used in this case is an excess of p-xylene. After working up with water and hydrochloric acid by known methods of organic chemistry, the organic phase (=solution of 2-chloro-1-(2,5-dimethylphenyl)ethanone in xylene) is employed in the next stage.

In the second step of the method of the invention, the solution of 2-chloro-1-(2,5-dimethylphenyl)ethanone in xylene is mixed with neopentyl glycol and a catalytic amount of p-toluenesulfonic acid. The mixture is then heated to reflux with a water trap until at least the expected theoretical amount of water has been removed. The reaction mixture can be employed in the next stage without further working up.

In one embodiment of the third step of the method of the invention, the solution of 2-chloromethyl-5,5-dimethyl-2-(2,5-dimethylphenyl)-[1,3]dioxane in xylene is first mixed with sodium acetate. Subsequently, ethylene glycol is added, and then the xylene is distilled off until a reaction temperature of about 180 to 190° C. is reached. This temperature is maintained for 4 to 7 hours. The reaction mixture is then allowed to cool to about 90° C. and employed in the next stage without further working up.

In one embodiment of the fourth step of the method of the invention for preparing 2,5-dimethylphenylacetic acid, the reaction mixture from the third stage is mixed at about 90 to 95° C. with sodium hydroxide solution and heated at 100 to 105° C. for 1 to 2 hours. The reaction mixture is then allowed to cool to room temperature, mixed with water, acidified by adding an acid such as, for example, hydrochloric or sulfuric acid, and then the 2,5-dimethylphenylacetic acid is isolated by filtration. The 2,5-dimethylphenylacetic acid is obtained in high yield and purity by washing with water and subsequent drying by conventional methods.

Preparation of 2,5-dimethylphenylacetic acid by the method of the invention is to be illustrated by the following preparation examples:

PREPARATION EXAMPLES FOR THE INDIVIDUAL STAGES

Example 1

2-Chloro-1-(2,5-dimethylphenyl)ethanone

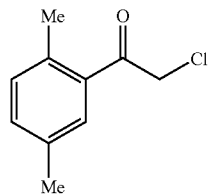

293.2 g [2.2 mol] of aluminum chloride are metered over the course of about 75 minutes into a mixture of 800 g p-xylene and 226 g [2 mol] of chloroacetyl chloride at 12-15° C. The reaction mixture is stirred at 12-15° C. for 2 hours, allowed to reach room temperature, stirred at room temperature for 30 minutes and then poured into 3000 ml of ice-water with 70 g of conc. hydrochloric acid. The cloudy organic phase is separated off, and the aqueous phase is extracted three times with 300 ml of ethyl acetate each time, and the combined organic phases are extracted twice with 200 ml of water each time and once with 100 ml of saturated aqueous NaCl solution. The organic phase is dried, evaporated and distilled as far as a bath temperature of 70° C./1 mbar. 363.6 g of yellowish oil result and, according to GC, contain 97.2% target product (96.8% of theory).

$^1$H-NMR (400 MHz, CDCl$_3$): δ=2.37 (s, 3H), 2.47 (s, 3H), 4.63 (s, 2H), 7.06 (d, 7.8 Hz, 1H), 7.23-7.26 (m, 1H), 7.4 (s, 1H) ppm.

Example 2

2-Chloromethyl-5,5-dimethyl-2-(2,5-dimethylphenyl)-[1,3]dioxane

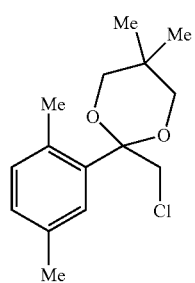

0.5 mol of 2-chloro-1-(2,5-dimethylphenyl)ethanone, 104 g [1 mol] of 2,2-dimethyl-1,3-propanediol (neopentyl glycol) and 9.5 g [0.05 mol] of p-TsOH hydrate are boiled in 500 ml of xylene with a water trap until the formation of water ceases (about 4 hours). 200 ml of water and 30 ml of xylene are added to the reaction mixture at room temperature. A better phase separation is achieved by adding 50 ml of saturated aqueous NaCl solution. The organic phase is then extracted again with 100 ml of water and 100 ml of saturated aqueous NaCl solution, dried and concentrated.

An oil is obtained and crystallizes after pouring onto a plate. Yield: 136.5 g with, according to GC, 93.1% target product (94.6% of theory).

$^1$H-NMR (400 MHz, CDCl$_3$): δ=0.62 (s, 3H), 1.37 (s, 3H), 2.34 (s, 3H), 2.37 (s, 3H), 3.43-3.52 (m, 4H), 3.59 (s, 2H), 7.06-7.10 (m, 2H), 7.30 (s, 1H) ppm.

Melting point: 80.5-81.5° C.

Example 3

2,5-Dimethylphenylacetic acid

A mixture of 4.1 g [0.05 mol] of sodium acetate and 10.75 g [0.04 mol] of 2-chloromethyl-5,5-dimethyl-2-(2,5-dimethylphenyl)-[1,3]dioxane in 50 ml of ethylene glycol is heated at 180 to 185° C. for 5 hours. It is then allowed to cool to 90 to 95° C., 20 ml of 30% strength sodium hydroxide solution are added, and the mixture is heated at 100 to 105° C. for 1 hour. The reaction mixture is diluted with 80 ml of water at room temperature and extracted twice with 10 ml of methylene chloride each time. The aqueous phase is then adjusted to pH 1 with conc. hydrochloric acid, and the solid is filtered off with suction, washed twice with 20 ml of water each time and dried. 6.20 g of white solid are obtained with a purity of 99.3% (GC). The yield is thus 93.7% of theory.

Example 4

2-Chloromethyl-2-(2,5-dimethylphenyl)-[1,3]-dioxolane

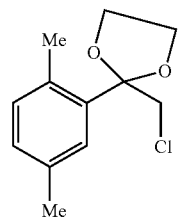

A mixture of 18.3 g [0.1 mol] of 2-chloro-1-(2,5-dimethylphenyl)ethanone, 12.6 g [0.2 mol] of ethylene glycol, 1.9 g [0.01 mol] of p-TsOH hydrate and 100 ml of xylene is heated to boiling with a water trap for about 3 hours. 40 ml of water and 20 ml of saturated aqueous NaCl solution are then added to the reaction mixture at room temperature. After addition of 20 ml of xylene, the organic phase is separated off and extracted with 20 ml each of water and saturated aqueous NaCl solution. The organic phase is dried over sodium sulfate and concentrated in vacuo. 18.35 g of oil result with, according to GC, 95.3% product (77.2% of theory).

GC/MS: m/e=226 (M$^+$ with $^{35}$Cl, <1%), 177 (M—CH$_2$Cl, 100%), 133 (177—OCH$_2$CH$_2$, 50%), 105 (133—CO, 20%).

Example 5

2-Chloromethyl-2-(2,5-dimethylphenyl)-[1,3]dioxane

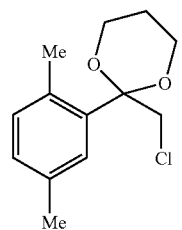

A mixture of 18.3 g [0.1 mol] of 2-chloro-1-(2,5-dimethylphenyl)ethanone, 15.2 g [0.2 mol] of trimethylene glycol, 1.9 g [0.01 mol] of p-TsOH hydrate and 150 ml of xylene is heated to boiling with a water trap for about 5 hours. Part of the xylene is then distilled off, and the reaction mixture is extracted at room temperature with 30 ml of saturated aqueous NaCl solution and twice with 100 ml of water each time. The organic phase is dried over sodium sulfate and concentrated in vacuo, and all volatiles are distilled off up to about 87° C. under 0.25 mbar. 22.9 g of residue remain with, according to GC, 83.9% product (79.8% of theory).

GC/MS: m/e=240 (M$^+$ with $^{35}$Cl, <1%), 191 (M—CH$_2$Cl, 100%), 133 (177—OCH$_2$CH$_2$CH$_2$, 100%), 105 (133—CO, 25%).

Example 6

2-Chloromethyl-4-methyl-2-(2,5-dimethylphenyl)-[1,3]dioxolane

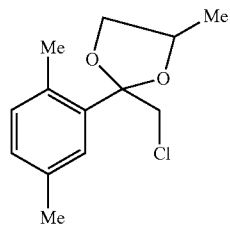

A mixture of 36.5 g [0.2 mol] of 2-chloro-1-(2,5-dimethylphenyl)ethanone, 22.8 g [0.3 mol] of propylene glycol, 3.6 g [0.02 mol] of p-TsOH hydrate and 150 ml of xylene is heated to boiling with a water trap for about 1.5 hours. Part of the xylene is then distilled off, and the reaction mixture is extracted at room temperature twice with 100 ml of water each time. The organic phase is dried over sodium sulfate and concentrated in vacuo, and volatiles are distilled off up to about 50° C./0.2 mbar. 39.65 g of an orange-colored oil remain with, according to GC, 93.0% product (76.7% of theory).

GC/MS: m/e=240 ($M^+$ with $^{35}Cl$, <1%), 191 (M—$CH_2Cl$, 90%), 133 (177—$OCH_2CHMe$—, 100%), 105 (133—CO, 25%).

Example 7

Carrying Out the Method of the Invention with Potassium Acetate in 4 Steps

1st Step 146.6 g [1.1 mol] of $AlCl_3$ are introduced over the course of 70 minutes into a mixture of 400 g of p-xylene and 113 g [1 mol] of chloroacetyl chloride at 20-25° C. The reaction mixture is stirred at 20-25° C. for 2 hours and then 750 ml of ice-cold water and 35 g of conc. hydrochloric acid are added. After stirring for 30 minutes, the organic phase is separated off and employed in the 2nd step.

2nd Step

The organic phase from the 1st step (469.2 g) is mixed with 135.5 g [1.3 mol] of neopentyl glycol and 19 g [0.1 mol] of p-toluenesulfonic acid hydrate. The mixture is heated to reflux with a water trap for about 6 hours, during which about 34 ml of aqueous phase are removed. In addition, about 340 ml of xylene are distilled out. The mixture is then employed in the 3rd step without further working up.

3rd Step

The still hot and liquid reaction mixture from the 2nd step is mixed with 137.4 g [1.4 mol] of potassium acetate and 1250 ml of ethylene glycol. It is then heated at 183 to 189° C. for 5 hours, during which small amounts of distillate are removed. The mixture is then employed in the 4th step without further working up.

4th Step

The reaction mixture from the 3rd step is allowed to cool to 90 to 95° C., mixed with 500 ml of 30% strength sodium hydroxide solution and heated at 100 to 105° C. for 1 hour. The reaction mixture is then diluted with 2000 ml of water and extracted twice with 150 ml of methylene chloride each time. The organic phase is then adjusted to pH 1 with conc. hydrochloric acid, and the precipitated solid is filtered off with suction, washed twice with 500 ml of water each time and dried. 117 g of solid are obtained with a GC purity of 95.2%. The yield is thus 67.5% of theory over 4 steps, i.e. on average about 90 to 91% in each stage.

Example 8

Carrying Out the Method of the Invention with Catalytic Amount of Sodium Acetate and Sodium Hydroxide Solution in 3 Steps 1st Step 146.6 g [1.1 mol] of $AlCl_3$ are introduced over the course of 70 minutes into a mixture of 400 g of p-xylene and 113 g [1 mol] of chloroacetyl chloride at 20-25° C. The reaction mixture is stirred at 20-25° C. for 2 hours and then 750 ml of ice-cold water and 35 g of conc. hydrochloric acid are added. After stirring for 30 minutes, the organic phase is separated off and employed in the 2nd step.

2nd Step

The organic phase from the 1st step (473.2 g) is mixed with 135.5 g [1.3 mol] of neopentyl glycol and 19 g [0.1 mol] of p-toluenesulfonic acid hydrate. The mixture is heated to reflux with a water trap for about 6 hours, during which about 29 ml of aqueous phase are removed. The mixture is then employed in the 3rd step without further working up.

3rd Step

The mixture from the 2nd step is mixed with 16.4 g [0.2 mol] of sodium acetate. After stirring at room temperature for 30 minutes, 1250 ml of ethylene glycol are added. The mixture is heated to boiling under 150 to 170 mbar, and 295 g are distilled out. Subsequently, 30 ml of ethylene glycol and then 267 g of 30% strength sodium hydroxide solution [equivalent to 3 mol of NaOH] are added. The reaction mixture is heated in an autoclave under autogenous pressure at 190 to 195° C. for 6 hours. After cooling to room temperature, the autoclave is emptied and the reaction mixture is diluted with 2500 ml of water. It is extracted three times with 300 ml of methyl tertiary-butyl ether (MTBE) each time, and the aqueous phase is then adjusted to pH 1 with conc. hydrochloric acid. The precipitated solid is filtered off with suction, washed twice with 1000 ml of water each time and dried. 124.4 g of white solid with a purity of 96.9% are obtained. This is a yield of 73.4% of theory over 3 steps, i.e. on average about 90% of theory per step.

Example 9

Carrying Out the Method of the Invention with Sodium Hydroxide Solution in 3 Steps 1st Step 146.6 g [1.1 mol] of $AlCl_3$ are introduced over the course of 60 minutes into a mixture of 400 g of p-xylene and 113 g [1 mol] of chloroacetyl chloride at 20-25° C. The reaction mixture is stirred at 20-25° C. for 2 hours and then 750 ml of ice-cold water and 35 g of conc. hydrochloric acid are added. After stirring for 30 minutes, the organic phase is separated off and employed in the 2nd step.

2nd Step

The organic phase from the 1st step (476.7 g) is mixed with 135.5 g [1.3 mol] of neopentyl glycol and 19 g [0.1 mol] of p-toluenesulfonic acid hydrate. The mixture is heated to reflux with a water trap for about 7 hours, during which about 37 ml of aqueous phase are removed. Then 315.8 g of distillate are removed in vacuo. The residue is then employed in the 3rd step.

3rd Step

The residue (315.6 g) obtained from the 2nd step is mixed with 1000 ml of ethylene glycol and 267 g of 45% strength sodium hydroxide solution [equivalent to 3 mol of NaOH]. The mixture is heated in an autoclave under autogenous pressure at 190 to 195° C. for 6 hours. The reaction mixture is then diluted with 2500 ml of water at room temperature. It is extracted three times with 300 ml of MTBE each time, the aqueous phase is adjusted to pH 1 with conc. hydrochloric acid, and the solid is filtered off with suction. Washing twice with 1000 ml of water each time and drying result in 139.7 g of solid with a GC purity of 99%. The yield resulting from this is 84.2% of theory over 3 steps, i.e. on average about 94.5% of theory per step.

The invention claimed is:

1. A compound of the formula (III)

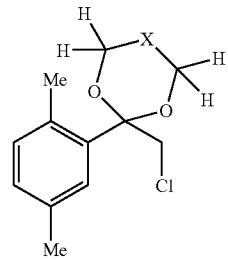

in which

X X is a direct single bond, $CH_2$ $CHCH_3$, $C(CH_3)_2$ or $C(C_2H_5)_2$.

* * * * *